US000001339H

United States Statutory Invention Registration [19]

[11] Reg. Number: H1339

Blair

[43] Published: Jul. 5, 1994

[54] AQUEOUS PROCESS FOR RECYCLING ACETAL POLYMER AND MOLDINGS THEREOF

[76] Inventor: Leslie M. Blair, 42 Lake Dr., Parkersburg, W. Va. 26101

[21] Appl. No.: 893,064

[22] Filed: Jun. 3, 1992

[51] Int. Cl.[5] ..... C08G 2/00
[52] U.S. Cl. ..... 528/230; 549/368
[58] Field of Search ..... 549/368; 568/457; 528/230

[56] References Cited

U.S. PATENT DOCUMENTS

| | | | |
|---|---|---|---|
| 3,000,960 | 9/1961 | Wheeler et al. | 568/457 |
| 3,409,675 | 11/1968 | Atwood et al. | 568/457 |
| 3,494,958 | 2/1970 | Mannsfeld et al. | 560/216 |
| 3,597,396 | 8/1971 | Ackermann et al. | 525/400 |
| 4,088,818 | 5/1978 | Radici et al. | 544/186 |
| 4,740,637 | 4/1988 | DelMar et al. | 568/807 |
| 5,043,121 | 8/1991 | Wingefeld et al. | 264/82 |

FOREIGN PATENT DOCUMENTS

| | | | |
|---|---|---|---|
| 858169-A | 12/1977 | Belgium . | |
| 138472-A | 11/1979 | Fed. Rep. of Germany . | |
| 0484786A1 | 5/1992 | Fed. Rep. of Germany . | |
| 48-024371-B | 7/1973 | Japan . | |
| 49-086311-A | 8/1974 | Japan . | |
| 49-086312-A | 8/1974 | Japan . | |
| 58-180515-A | 10/1983 | Japan . | |
| 60-260538-A | 12/1985 | Japan . | |
| 1502560 | 8/1989 | U.S.S.R. | 568/457 |
| 1363928-A | 8/1974 | United Kingdom . | |

*Primary Examiner*—Robert L. Stoll
*Assistant Examiner*—Joseph D. Anthony

[57] ABSTRACT

This invention relates to an aqueous process for recycling polyacetal, and moldings thereof, into formaldehyde monomer solution, said process occurring at elevated temperature and pressure and in the presence of an acid decomposition catalyst, such as sulfuric acid. The resultant formaldehyde monomer solution can be reacted to form trioxane and then be cycled into a trioxane-based polyacetal manufacturing process or, alternatively, it can be further treated and then be cycled into a formaldehyde-monomer-based polyacetal manufacturing process.

11 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

AQUEOUS PROCESS FOR RECYCLING ACETAL POLYMER AND MOLDINGS THEREOF

BACKGROUND OF THE INVENTION

The present invention relates to an aqueous process for recycling acetal polymer, and moldings thereof, into formaldehyde monomer solution. The formaldehyde monomer solution may also contain formaldehyde trimer (hereinafter referred to as "trioxane").

Polyacetal resin is manufactured, in general, from formaldehyde monomer and/or trioxane. Formaldehyde-monomer-based polyacetal manufacturing processes are generally used to manufacture acetal homopolymers, while trioxane-based polyacetal manufacturing processes are generally used to manufacture acetal copolymers. Polyacetal resin is used in many applications and is molded into many types of products, such as disposable lighter bodies, ski bindings, conveyor chain links, gears, hinges, automotive window cranks, etc. After the useful life of such products expire, the product is scrapped, and becomes waste.

It is desirable, for economic and environmental reasons, to recycle polyacetal, and moldings thereof, back into the components from which it is manufactured, i.e., formaldehyde monomer and/or trioxane. One known way to recycle polyacetal is a gas phase recovery process, wherein the polyacetal is thermally decomposed with a catalyst to form formaldehyde monomer gas and then the gas is recycled directly into a polyacetal manufacturing process. Unfortunately, it has been found that the formaldehyde monomer gas generated by such a process may contain traces of volatile base products, such as, for example, amine compounds or possibly ammonia. When the formaldehyde monomer gas is recycled into a polyacetal manufacturing process, it can make the process inoperable by initiating polymerization in the wrong places. Furthermore, the yield obtained by the gas phase process is sometimes lower than desired. Thus, there exists a need to develop new and efficient means for recycling polyacetal resin into its monomeric formaldehyde and/or trioxane components, wherein said components are acceptable for use in an actual polyacetal manufacturing process.

In the present invention, there has been developed an aqueous process, done in the presence of an acid decomposition catalyst, for recycling polyacetal, and moldings thereof, into formaldehyde monomer solution. The formaldehyde monomer solution can, by the nature of the decomposition reaction, also contain trioxane. The resultant formaldehyde monomer solution is then treated (by, for example, filtration, neutralization, and purification processes) in preparation for cycling into formaldehyde-monomer-based polyacetal manufacturing processes. Alternatively, with or without further treatment, the resultant formaldehyde monomer solution can be reacted, either during the decomposition process or thereafter, to form trioxane, which in turn can be used in trioxane-based polyacetal manufacturing processes.

SUMMARY OF THE INVENTION

This invention relates to an aqueous process for recycling polyacetal, and moldings thereof, into formaldehyde monomer solution by heating, under pressure, a slurry of polyacetal, water, and an acid decomposition catalyst, such as sulfuric acid, until the polyacetal is dissolved (i.e., decomposed), thereby yielding a formaldehyde monomer solution. The formaldehyde monomer solution can be treated (by, for example, filtration, neutralization, and purification processes) in preparation for cycling into formaldehyde-monomer-based polyacetal manufacturing processes. Alteratively, the formaldehyde monomer solution can be reacted, either during the dissolution/decomposition process or thereafter, and either with or without further treatment, to form trioxane which, in turn, can be cycled into trioxane-based polyacetal manufacturing processes.

DETAILED DESCRIPTION OF THE INVENTION

The present invention relates to an aqueous catalytic process for recycling polyacetal, and moldings thereof, into a formaldehyde monomer solution. Specifically, in the process of the present invention, polyacetal is slurried in water in the presence of an acid decomposition catalyst. The slurry is then heated under pressure until the polyacetal therein is dissolved. The catalyst acts to decompose the polyacetal into formaldehyde monomer. The resulting solution is a solution of formaldehyde monomer. There may also be trioxane present in the solution due to the nature of the decomposition reaction; however, the solution will be predominantly formaldehyde monomer.

The term "polyacetal", or "acetal polymer", as used herein is meant to include acetal homopolymer, acetal copolymer, mixtures of acetal homopolymer and acetal copolymer, and moldings thereof. Acetal homopolymers and copolymers are well known in the art and are described in, for example, U.S. Pat. No. 5,011,890. Moldings prepared from polyacetal compositions may be used in the process described herein. In most cases, and especially when the process is used to recycle polyacetal, the polyacetal that is dissolved in water in the present process will be a molded polyacetal composition. It is understood that such moldings may contain ingredients normally added to polyacetal compositions, including, but not limited to, thermal stabilizers, antioxidants, UV stabilizers (including hindered amine light stabilizers), pigments, tougheners, fillers, glass, lubricants (such as silicone oil), polytetrafluoroethylene, and nucleants (such as talc or boron nitride). Further, such moldings may contain labels, metal parts, etc. which do not necessarily need to be removed before processing and which can be easily filtered out in later steps. When polyacetal moldings are used in the present process, it is recommended that the molding be coarsely crushed prior to slurrying it with water in order to aid in dissolution.

The polyacetal is added to the water to create a slurry. The concentration of the polyacetal in the slurry ranges from 5 to 90 percent by weight, preferably from 25 to 70 percent by weight, and most preferably (a) from 50 to 75 percent by weight if the formaldehyde monomer solution resulting from the slurry is to be reacted to form trioxane and (b) from 35 to 55 percent by weight if the formaldehyde monomer solution resulting from the slurry is to be cycled into a formaldehyde-monomer-based polyacetal manufacturing process. All percents in this paragraph are based upon the total weight of the polyacetal and water only. The process is applicable to slurries containing less than 5 weight percent polyacetal; however, using the present process with a slurry having low concentration of polyacetal is not very economic. The process is also applicable to slurries containing greater than 90 weight percent polyacetal; however, as the concentration of polyacetal in the slurry increases, operation of the process may become increasingly more difficult due to the need to maintain high solution temperatures in order to prevent substantial precipitation of solids from the solution.

A catalytic amount of an acid catalyst is used in the present process to decompose and thereby dissolve the polyacetal. Generally, very little catalyst is needed. High concentrations of catalyst may speed the dissolution/decomposition process, but may also create side reactions and require that the resultant solution be extensively neutralized at the end of the dissolution/decomposition process. It is generally recommended that not more than 10 parts acid catalyst to 90 parts water be used in the process herein. Preferably, there will be used 1–2 parts of acid catalyst per 100 parts of water. The amount of catalyst used should be enough to induce decomposition of the polyacetal, but not so much as to induce substantial side reactions and require extensive neutralization of the resultant solution.

Decomposition of polyacetal in an aqueous solution is acid catalyzed. The acid catalyst may be a strong acid or a weak acid and should not react adversely with the formaldehyde monomer being formed during the decomposition process. Strong acid catalysts are preferred because they induce higher rates of decomposition of the acetal polymer at lower composition levels and lower temperatures than weak acids. Examples of suitable strong acid catalysts include, but are not limited to, sulfuric acid, p-toluene sulfonic acid, and phosphoric acid, with sulfuric acid being most preferred. Examples of suitable weak acids include, but are not limited to, organic acids, such as formic acid and acetic acid.

The polyacetal, water, and catalyst are slurried together at room temperature and then heated under pressure to facilitate decomposition/dissolution at an economic and acceptable rate. Generally, the process can be conducted above the melting point of the polyacetal polymer, but preferably at not greater than 200° C. Temperatures below the melt processing temperature of the polyacetal are preferred. For acceptable and economic dissolution rates, it is generally recommended that the process herein be conducted in the range of 120° C. to 200° C., and most preferably in the range of 140° C.–160° C. Temperatures greater than 200° C., including up to 250° C., may be used so long as sufficient pressure is provided to the reaction and substantial side reactions do not occur. Temperatures lower than 120° C. can be used, but dissolution time may slow considerably, thereby resulting in a process that is not economically attractive.

The pressure under which the process is conducted is defined by the vapor pressure of the water at the temperature selected for reaction. For example, a pressure range of 14 psig to 210 psig corresponds to an operating temperature range of 120° C.–200° C., while a pressure range of 40–70 psig corresponds to an operating temperature range of 140° C.–160° C., and a pressure of 540 psig corresponds to an operating temperature of about 250° C.

The reaction proceeds at elevated temperature and pressure until the polyacetal is dissolved. Standards techniques can be used to determine whether or not the polyacetal is dissolved, including visual inspection or intermittent sampling of the solution being generated. The resultant solution contains formaldehyde monomer and various additives commonly included in polyacetal compositions or on polyacetal moldings; however, it contains predominantly formaldehyde monomer.

The resultant formaldehyde solution can be prepared for cycling into formaldehyde-monomer-based polyacetal manufacturing processes by subjecting it to further processing, such as filtration, neutralization, and purification processes.

Filtration can be done by standard techniques. Filtration is done to remove insoluble, non-acetal contamination (such as insoluble fillers, like $TiO_2$ and pigments) from the polyacetal resin and labels, stickers, metal caps, etc. from polyacetal molded parts.

Purification, especially to remove traces of volatile base products, such as amine compounds or ammonia, which can make the polyacetal manufacturing process inoperable by interfering with polymerization in the wrong places, can be done by purification techniques readily available to those skilled in the art. Examples of suitable purification techniques include ion exchange treatment and distillation/extraction techniques. Purification by ion exchange treatment is preferred for cost reasons. Traces of metal salts, which can reduce the efficiency and performance of the polyacetal manufacturing process by catalyzing undesirable side reactions, can also be removed by ion exchange treatment. Standard acid ion exchange resins, such as a sulfonated polystyrene ion exchange resin, are suitable for the ion exchange treatment.

It is recommended that the formaldehyde monomer solution be neutralized to remove any residual strong acid content that may act as an undesirable catalyst in the particular polyacetal manufacturing process into which the formaldehyde monomer solution will eventually be cycled. Neutralization can be done by standard techniques; it is most economically done after the formaldehyde monomer solution has been purified.

In many cases, polyacetal (and especially acetal copolymer) is prepared from trioxane-based polyacetal manufacturing processes. The filtered, purified, and neutralized formaldehyde monomer solution described above can be reacted to form trioxane by techniques readily available to those skilled in the art, such as distillation, and then recycled into the trioxane-based polyacetal manufacturing process.

Alternatively, trioxane can be formed from the formaldehyde monomer solution prior to the purification and neutralization thereof. In fact, as shown by the yields obtained in the Examples below, it is preferred, and more economically advantageous, to carry out the reaction of the formaldehyde monomer solution to trioxane in the presence of the metals, salts, and other contaminants existing in the formaldehyde monomer solution after the dissolution/decomposition process is complete. The resulting trioxane solution could then be purified by standard techniques (e.g., the trioxane is extracted from the aqueous solution by a hydrocarbon, such as benzene, and then purified by distillation). The purified trioxane product can then be recycled into a trioxane-based acetal manufacturing process. It has been found, as also shown in the Examples below, that the rate of trioxane production from polyacetal scrap, by the present process, was surprisingly greater than the rate of trioxane production from a solution of pure formaldehyde monomer.

The reaction to trioxane can be done in a reaction vessel separate from the one used for the dissolution/decomposition process or, more preferably and most economically, trioxane can be generated simultaneously with the dissolution/decomposition process by including an added distillation step.

The amount of formaldehyde monomer in solution at the end of the dissolution process can be determined by standard titration methods. The amount of trioxane in solution at the end of the reaction to trioxane can be determined by standard techniques of gas chromatography. The yield of formaldehyde per unit mass of acetal molding has been found to be generally greater than 90 percent by the present process.

The process of the present invention can be commercially practiced using batch reactors or using continuous reactors.

EXAMPLES

Unless otherwise specified, the "formaldehyde monomer content" values given in the Examples below were determined by standard techniques of direct sulfite titration.

The "tube" referred to in the Examples below was a 100 $cm^3$ glass-pressure tube equipped with a metal head consisting of valved inlet lines, exit vapor lines, and a pressure gauge.

Unless otherwise specified, the acetal homopolymer samples used in the Examples below contained generally less than about 2% additives.

EXAMPLE 1

A 2 gram sample of a brown acetal copolymer molding (Celcon®, sold by Hoechst Celanese) and six 2 gram samples of acetal homopolymer moldings of assorted colors (taken from BIC® disposable lighter bodies, which were made of Delrin® acetal homopolymer, manufactured by Du Pont Company) were coarsely crushed to about ¼" to ½" pieces, on average, and then added to the tube described above. Additionally, 28 grams of demineralized water and about 1 gram of sulfuric acid were added to the tube. Then, with some additional inert gas pressure (20 psig $CO_2$), the tube was inserted into an oil bath having a temperature of 160° C. The pressure inside the tube increased to 50 psig as the temperature of the liquid inside the tube increased to about 150° C.

After about 30 minutes in the oil bath, the polymer was completely dissolved, as determined by visual inspection. The formaldehyde monomer content in the resultant solution was 29.7 percent. The recovery of formaldehyde monomer was 91 percent, as based upon the initial weight of charged polyacetal scrap.

The solution inside the tube, which had a pH of about 2.6, was filtered and neutralized with a 20% sodium hydroxide solution, until the pH of the solution was about 9. The neutralized solution was then purified by passing it through a sulfonic acid resin ion exchange bed (Ionac C-242®, H+ form), giving the reductions in impurity levels indicated in TABLE A, below. The resultant purified solution was pure enough to cycle into an acetal manufacturing process.

TABLE A

| Impurity | Before Ion Exchange (ppm) | After Ion Exchange (ppm) |
|---|---|---|
| N | 25 | 0.1 |
| Na | 5600 | 2 |
| Ca | 53 | 1 |
| Ni | 5 | 0 |
| Zn | 1 | 0 |
| Mn | 1 | 0 |
| Fe | <1 | 0 |
| Cu | <1 | 0 |

COMPARATIVE EXAMPLE 1-A

The experiment described below relates to a gas-phase process for the recovery of formaldehyde monomer from solid acetal scrap.

Five grams of Delrin® acetal homopolymer fluff (which contained no additives), 50 ml of hexadecane solvent, and 1 gram of para-toluene sulfonic acid were added to a 500 ml round bottom flask, wrapped with insulation, equipped with an electrical resistance beater, magnetic stirrer, thermometer, an inlet line, and an exit line. Under nitrogen flow, the components were mixed together and heated, over a period of about 25 minutes and up to 160° C., until all of the polymer was dissolved.

The nitrogen that was metered into the flask through the inlet line swept the formaldehyde gas generated during heating through the exit line to a water-filled gas washing bottle. After dissolution, a large amount of black solid deposits remained at the bottom of the flask after heating was terminated. The amount of formaldehyde monomer gas recovered in the gas washing bottle, as measured by standard sulfite titration techniques, was found to be 1.25 grams, or only 25 percent of the original polyacetal weight charged to the flask.

EXAMPLE 2

A white BIC® lighter body (which was made of a Delrin® acetal homopolymer manufactured by Du Pont), including the red valve, was broken and ground into a fine powder. Two grams of the ground powder, four grams of demineralized water, and four drops of sulfuric acid were added to the tube described above. The tube was pressurized with carbon dioxide to 20 psig and then placed into a 160° C. oil bath. Pressure increased to about 50 psig over a period of 30 minutes, while the temperature inside the bomb varied from 125° C. to 145° C. By visual inspection, most of the polymer was dissolved within 25 minutes. Heating was continued for a total of about 110 minutes, although a heating time of 30 minutes appeared to be sufficient to dissolve the polymer. The resultant solution was filtered. The formaldehyde monomer content in the resultant solution was 26.6 percent. Thus, 1.64 grams of formaldehyde monomer were generated from 2.0 grams of acetal scrap (82 percent recovery).

EXAMPLE 3

A brown Celcon® acetal copolymer molding was ground into a fine powder. Two grams of the ground powder, 4.4 grams of demineralized water, and 4 drops of sulfuric acid were added to the tube described above. The tube was pressurized with carbon dioxide to 20 psig and then placed into a 160° C. oil bath. Over the next 25 minutes, pressure increased to 50 psig as temperature increased to 145° C. The formaldehyde monomer content in the resultant solution, was 28.3 percent. Thus, 1.85 grams of formaldehyde monomer were recovered from 2 grams of acetal scrap (92.5 percent recovery).

EXAMPLE 4

A green BIC® disposable lighter body (which was made of Delrin® acetal homopolymer) was broken into ¼"–½" pieces, on average. Two grams of the broken pieces, 4 grams of water, and 4 drops (0.17 grams) of $H_2SO_4$ were added to the tube described above. The tube was pressurized with carbon dioxide to 20 psig and placed in a 160° C. oil bath. Over the next 35 minutes, pressure increased to 57 psig as temperature increased to 150° C. The acetal scrap was substantially dissolved at the end of the 35 minutes, indicating that it was not necessary to grind the acetal scrap into a fine powder in order for dissolution to occur at an acceptable rate.

EXAMPLE 5

The Example 5 series of experiments relate to conversion of formaldehyde monomer solution to trioxane.

EXAMPLE 5A

A 28 gram charge of the same mixed acetal scrap referred to in Example 1 was added to the tube described above, along with 22 grams of demineralized water and one gram of sulfuric acid. Dissolution of the acetal scrap in water was carried out in a similar manner as described for Example 1. The resultant solution was filtered to yield a solution that was purplish in color. The filtered solution was then added to a 250 ml reaction flask equipped with a magnetic stirrer, heater, and a distillation head with a condensate takeoff. The solution was distilled at atmospheric pressure and at a pot temperature of 99° C. for about 90 minutes. The first 25 ml of condensate were collected. The condensate contained 19.6 percent trioxane (determined by gas chromatography). The formaldehyde monomer content in the condensate was 31.9 percent. Thus, for a condensate density of 1.1 g/ml, 5.3 grams of trioxane were made from 28 grams of acetal scrap.

EXAMPLE 5B 28 grams of cubes of a Delrin ® acetal homopolymer, manufactured by Du Pont, were charged to the tube described above, along with 22 grams of demineralized water and 1 gram of sulfuric acid. The tube was pressurized and the acetal homopolymer cubes were dissolved as in Example 1 (55 minute dissolution time, temperature to about 140° C.). As in Example 5A, the solution was filtered and then distilled at a pot temperature of about 99.5° C. for approximately 90 minutes. The first 25 ml of condensate were collected. The formaldehyde monomer content in the condensate was 33.6 percent. The trioxane content in the condensate was 16.9 percent (determined by gas chromatography). Thus, 4.6 grams of trioxane were formed from the 28 gram charge of Delrin ® acetal homopolymer cubes.

EXAMPLE 5C

EXAMPLE 5B was repeated except that 5 grams of sulfuric acid were charged into the reactor flask instead of 1 gram of sulfuric acid. The results are given in TABLE B, below.

Comparative Example 5A ("C-5A")

A comparative example was conducted wherein 50 grams of a pure 55 percent aqueous formaldehyde solution were charged to the same reaction flask/distillation apparatus of Example 5A, along with 1 gram of sulfuric acid. Reaction and distillation processes were carried out in the same manner as described in Example 5A. As in Example 5A, the first 25 ml of condensate were collected. The content of trioxane in the condensate was only 2.9 percent. Thus, only 0.8 grams of trioxane were made from 27.5 grams of pure formaldehyde. The formaldehyde monomer content in the condensate was 37.9 percent.

COMPARATIVE EXAMPLE 5B ("C-5B")

Comparative Example 5A was repeated except that 5 grams of sulfuric acid were charged into the reaction flask instead of 1 gram of sulfuric acid. The results are given in TABLE B, below.

The results of Examples 5A, 5B, and 5C, along with the results of Comparative Examples 5A and 5B, are summarized in TABLE B, below.

TABLE B

| Example No. | Acetal Feed Condition | $H_2SO_4$ (1) (g) | Initial Formaldehyde Charge (2) (g) | Formaldehyde Monomer Content in Condensate (wt %) | Trioxane Content in Condensate (wt %) | Wt. of Trioxane in Condensate (g) |
|---|---|---|---|---|---|---|
| 5A | Mixed acetal scrap | 1 | 27.4 | 31.9 | 19.6 | 5.3 |
| 5B | Acetal homopolymer cubes | 1 | 27.4 | 33.6 | 16.9 | 4.6 |
| 5C | Acetal homopolymer cubes | 5 | 27.4 | 19.6 | 21.3 | 5.9 |
| *C-5A | 55% pure formaldehyde | 1 | 27.5 | 37.9 | 2.9 | 0.8 |
| *C-5B | 55% pure formaldehyde | 5 | 27.5 | 33.8 | 6.3 | 1.7 |

*Comparative example
(1) Sulfuric Acid
(2) As based upon 98% formaldehyde in the polyacetal sample

I claim:

1. An aqueous process for recycling acetal polymer, and moldings thereof, into a formaldehyde monomer solution by heating, under pressure, a slurry of at least one acetylpolymer, water, and an acid decomposition catalyst until the acetyl polymer is dissolved, thereby resulting in a solution comprised of formaldehyde monomer.

2. The process of claim 1 wherein the acid decomposition catalyst is selected from the group consisting of sulfuric acid, p-toluene sulfonic acid, phosphoric acid, acetic acid, and formic acid.

3. The process of claim 1 wherein the slurry is heated in the range of 140° C. to 160° C. under corresponding pressures ranging from 40 psig to 70 psig.

4. The process of claim 1 wherein the acetal polymer is selecting form the group consisting of acetal homopolymer, acetal copolymer, mixtures of acetal homopolymer and acetal copolymer.

5. The process of claim 1 wherein the acetal polymer is selected from moldings of acetal homopolymer, moldings of acetal copolymer, and moldings of mixtures of acetal homopolymers and acetal copolymers.

6. The process of claim 1 wherein the acetal polymer additionally contains at least one of thermal stabilizers, antioxidants, UV stabilizers, pigments, tougheners, fillers, glass, lubricants, polytetrafluoroethylene, and nucleants.

7. The process of claim 1 wherein the resultant formaldehyde monomer solutions is filtered, purified, and neutralized and then cycled into a formaldehyde-monomer-based polyacetal manufacturing process.

8. The process of claim 7 wherein the formaldehyde monomer solution is purified by passing it through an ion exchange bed.

9. The process of claim 1 wherein the resultant formaldehyde monomer solution is reacted to form a trioxane solution.

10. The process of claim 9 wherein the reaction to form trioxane occurs simultaneously with the dissolution of the acetal polymer, said reaction to trioxane occurring by a distillation step.

11. The process of claim 9 wherein the trioxane solution is purified and cycled into a trioxane-based acetal manufacturing process.

* * * * *